US00RE45664E

(19) United States
(12) Reissued Patent
Hubbard et al.

(10) Patent Number: US RE45,664 E
(45) Date of Reissued Patent: Sep. 8, 2015

(54) SYSTEM FOR MEASURING AND INDICATING CHANGES IN THE RESISTANCE OF A LIVING BODY

(71) Applicants: Norman F. Starkey, Los Angeles, CA (US); Church of Spiritual Technology, Los Angeles, CA (US)

(72) Inventors: Lafayette Ron Hubbard, Los Angeles, CA (US); Richard Stinnett, Corona, CA (US); Trent Lillihaugen, Camarillo, CA (US); John Temples, Camarillo, CA (US)

(73) Assignee: Church of Spiritual Technology, Los Angeles, CA (US)

(21) Appl. No.: 13/850,962

(22) Filed: Mar. 26, 2013

Related U.S. Patent Documents

Reissue of:
(64) Patent No.: 8,121,676
Issued: Feb. 21, 2012
Appl. No.: 10/549,649
PCT Filed: Mar. 19, 2004
PCT No.: PCT/US2004/006084
§ 371 (c)(1),
(2) Date: Mar. 15, 2007
PCT Pub. No.: WO2004/094955
PCT Pub. Date: Nov. 4, 2004

U.S. Applications:
(60) Provisional application No. 60/455,948, filed on Mar. 19, 2003.

(51) Int. Cl.
*A61B 5/00* (2006.01)
*A61B 5/05* (2006.01)
*A61B 5/053* (2006.01)

(52) U.S. Cl.
CPC ..... *A61B 5/053* (2013.01)

(58) Field of Classification Search
USPC ..... 600/300, 535, 547
See application file for complete search history.

(56) References Cited

U.S. PATENT DOCUMENTS 3,557,352 A * 1/1971 Hogg et al. ..... 702/29
4,578,635 A 3/1986 Mee (Continued)

FOREIGN PATENT DOCUMENTS

JP 2001-000411 A 1/2001
JP 2001-1074795 A 3/2001

(Continued)

*Primary Examiner* — Sean Dougherty
(74) *Attorney, Agent, or Firm* — Robert A. Seldon

(57) ABSTRACT

An improved device for indicating and measuring small variations in the resistance of a living body is disclosed which utilizes a central processing unit to digitally process sensed body resistances and drive a resistance-indicating display while compensating for the effects of component aging, component tolerances and component temperatures. The device includes an automatic calibration circuit that is automatically activated on each powering up of the device to measure and store measurement values for a plurality of synthesized body resistances that are used to form a compensation model against which sensed body resistances are, subsequently compared for automatic adjustment of display driving measurement values. The central processing unit additionally adjusts the gain of the meter-driving signal by a gain factor dependant on a user-selected meter-sensitivity setting to avoid previously experienced difficulties in monitoring small changes in body resistance caused by difficulty in setting the initially desired meter reading at certain meter-range values, as well as occasional false and unexpected reversals of meter reading as the meter's range was adjusted.

24 Claims, 10 Drawing Sheets

(56) References Cited

U.S. PATENT DOCUMENTS

| | | | |
|---|---|---|---|
| 5,372,141 | A | 12/1994 | Gallup |
| 6,011,992 | A | 1/2000 | Hubbard |

FOREIGN PATENT DOCUMENTS

| | | | |
|---|---|---|---|
| JP | 2001-178844 | A | 7/2001 |
| JP | 2002-253522 | A | 9/2002 |

* cited by examiner

FIG. 5
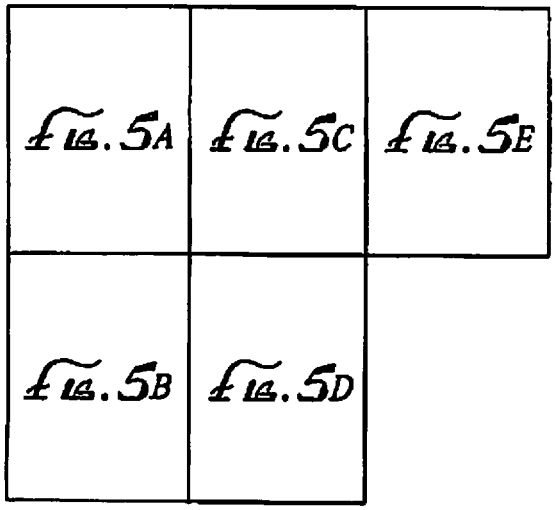
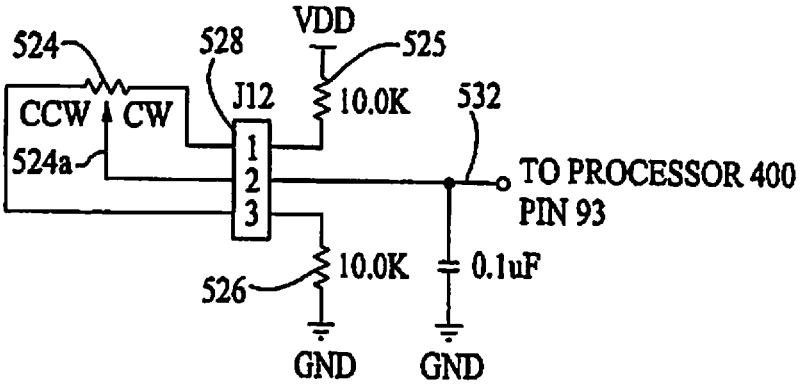
FIG. 6

SYSTEM FOR MEASURING AND INDICATING CHANGES IN THE RESISTANCE OF A LIVING BODY

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

This application claims the priority of U.S. Provisional Application No. 60/455,948 filed Mar. 19, 2003.

This invention relates to an improved device for indicating and measuring variations in the resistance of a living body.

BACKGROUND

Devices for measuring and displaying small changes in the resistance of a living body have previously been disclosed in U.S. Pat. Nos. 3,290,589 and 4,459,995 as well as U.S. Pat. No. 6,011,992. These devices generally include a resistance measuring circuit, an amplifier circuit and an indicator circuit. In operation, the device measures the small resistance changes utilizing the resistance measuring circuit to generate a measurement signal indicative of the magnitude of resistance. The measurement signal is then amplified by the amplifier circuit, and the amplified signal is used to drive a display such as an electromagnetically-responsive needle of a meter. The reliability of the readings has depended not only proper calibration of the device, but also on the accurate adjustment of circuit gains and sensitivities as the living body is monitored.

Devices of this type were first conceived and developed by inventor Hubbard for use in monitoring, or auditing, individuals as part of a counseling protocol. The devices are utilized to detect small changes in the electrical resistance of the audited person as that person looks at aspects of his own existence in order to improves his ability to confront what he is and where he is. The ability to detect and visually perceive the occurrences of very small, and sometimes quite fleeting, resistance changes as well as certain patterns of changes is essential to accurate and maximally effective auditing of the individual.

While the foregoing prior art devices have been suitable for detecting the resistance changes in the living body, they have been difficult to calibrate correctly and difficult to operate in a manner that consistently produces accurately perceived display readings. It appears that these difficulties arise from such characteristics as signal non-linearities, as well as age-related and temperature-related component changes that can mask or falsely report small but meaningful measurement changes.

Inventor Hubbard recognized that signal non-linearities were a significant factor that greatly complicated the reliable display of needed information, and that the interaction between range and sensitivity adjustments on such devices further complicated the ability to obtain clear readings. Mr. Hubbard further identified slight delays as small as 0.1 seconds in displaying resistance changes as a further source that complicated auditing and determined that the most effective display required even the smallest possible resistance changes to be perceived with as little delay as possible.

SUMMARY OF THE INVENTION

The invention herein is an improved device for measuring and indicating resistance and resistance changes in a living body. The device utilizes digital processing to improve display response and accuracy. An automatic calibration sequence substantially offsets the effects of component aging, temperature changes and manufacturing tolerances on these very sensitive measurements. Preferred circuitry for sensitivity adjustments isolates those adjustments from effecting the resistance measurement circuitry.

These and other features of the invention will be appreciated from the following description of the preferred embodiment, of which the drawings form a part.

THE DRAWINGS

Figure 1:
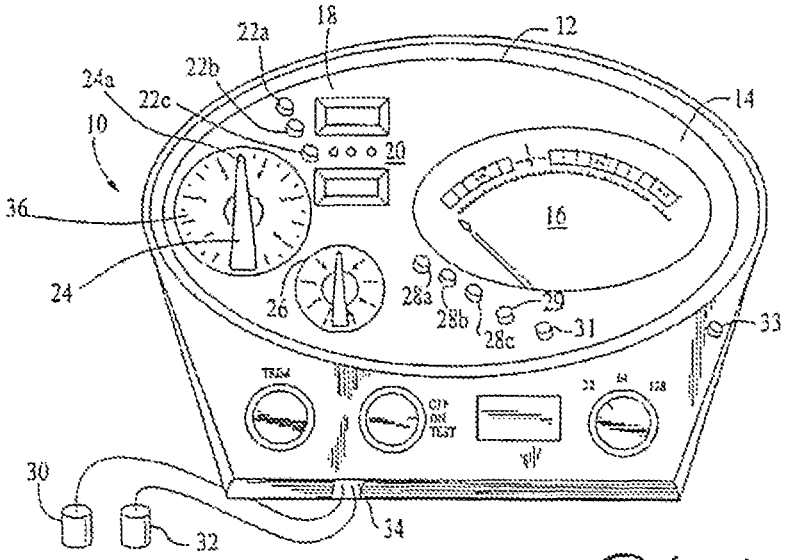
FIG. 1 is a front view in perspective of a preferred embodiment of a device for measuring and indicating changes in resistance of a living body that has been constructed in accordance with the invention.
Figure 3:
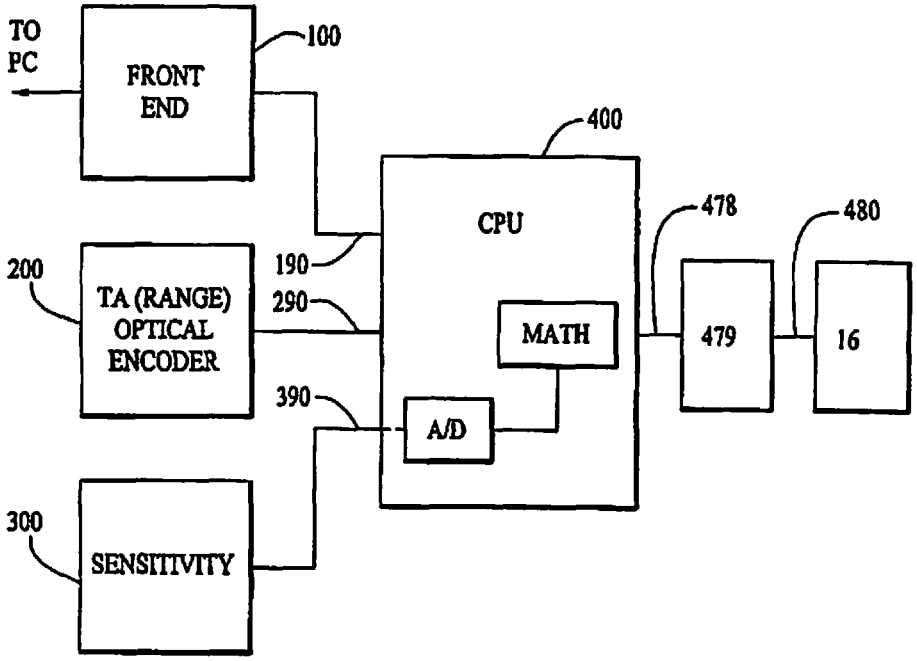
Figure 1:
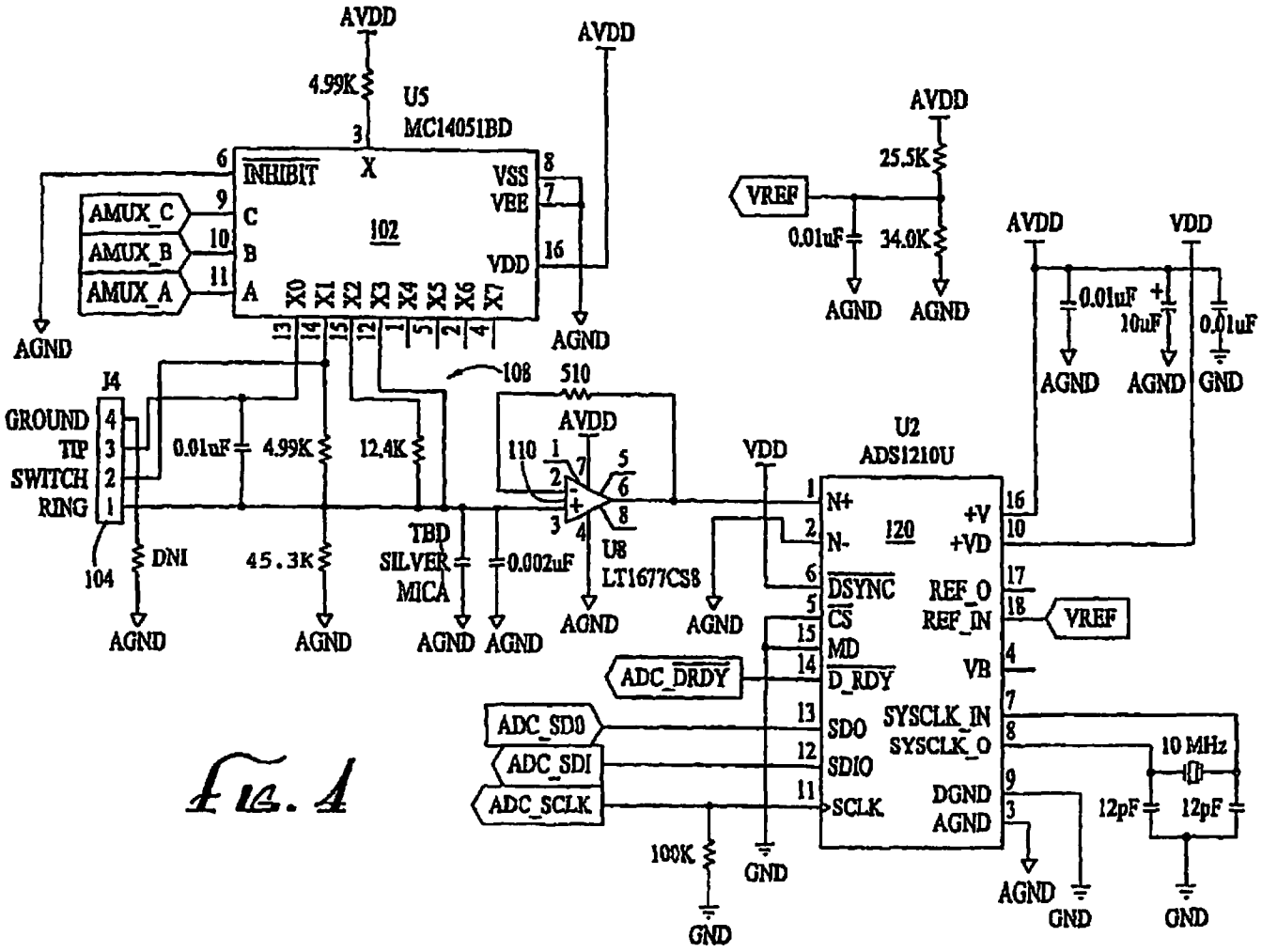
Figure 5A:
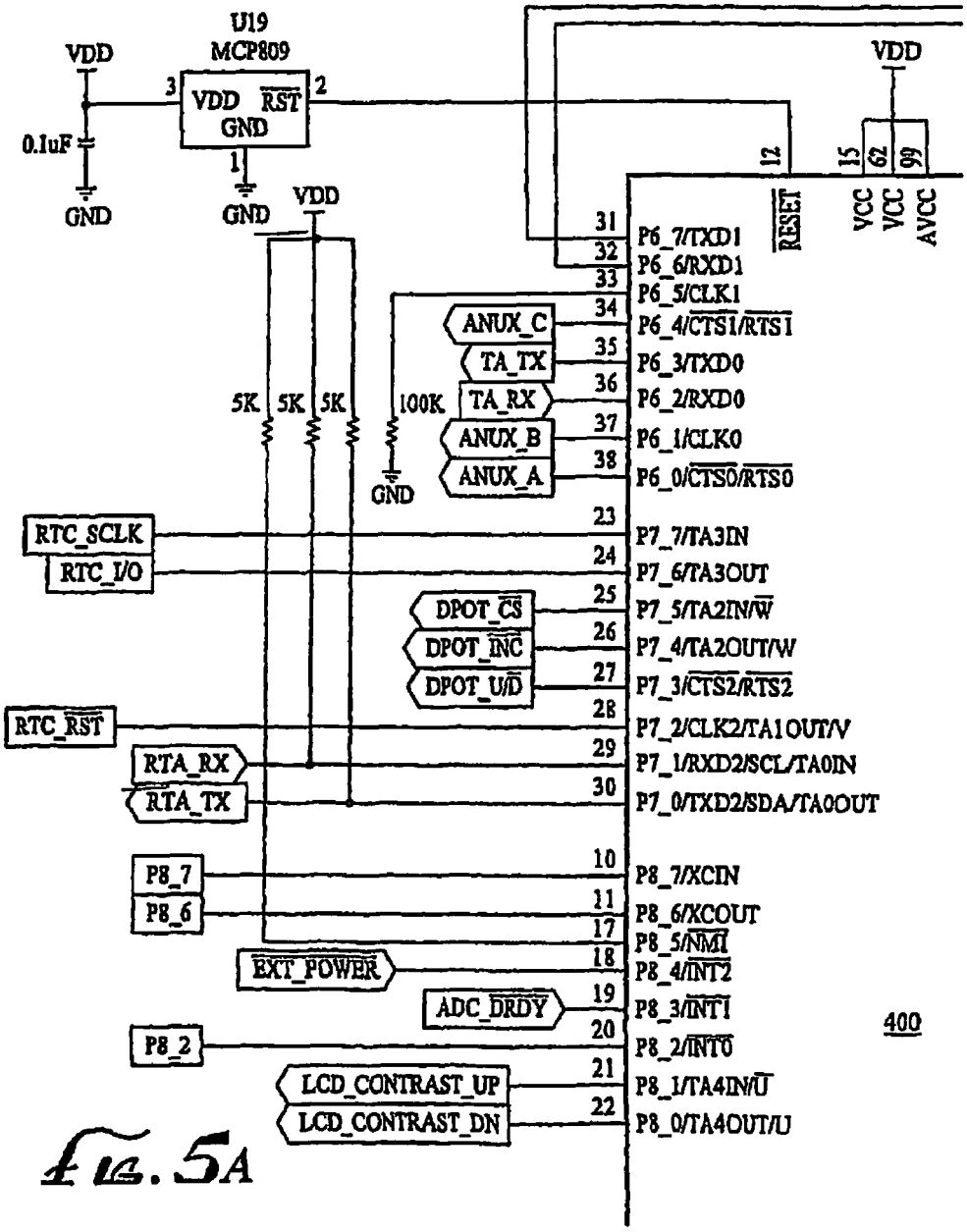
Figure 5B:
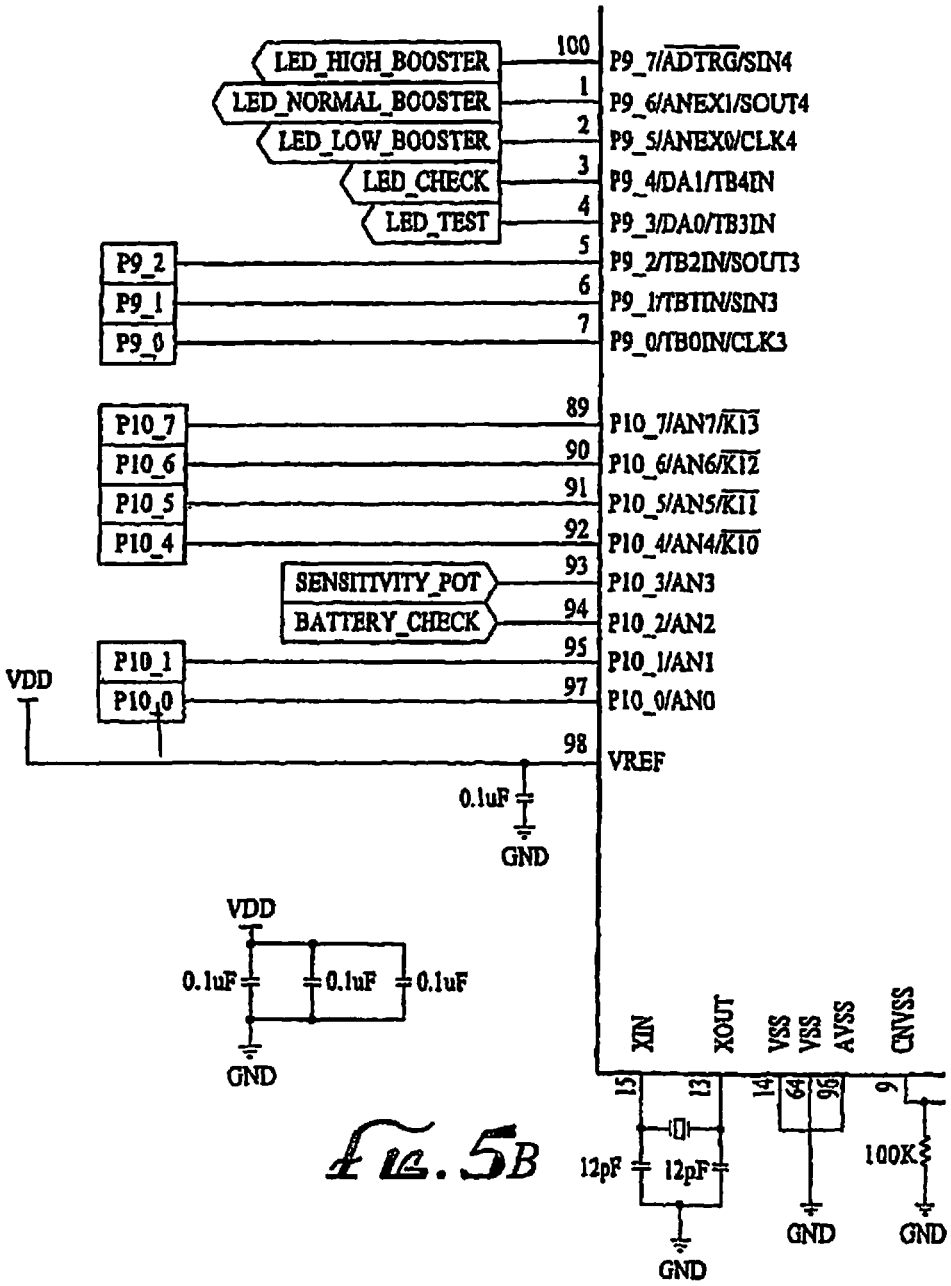
Figure 5C:
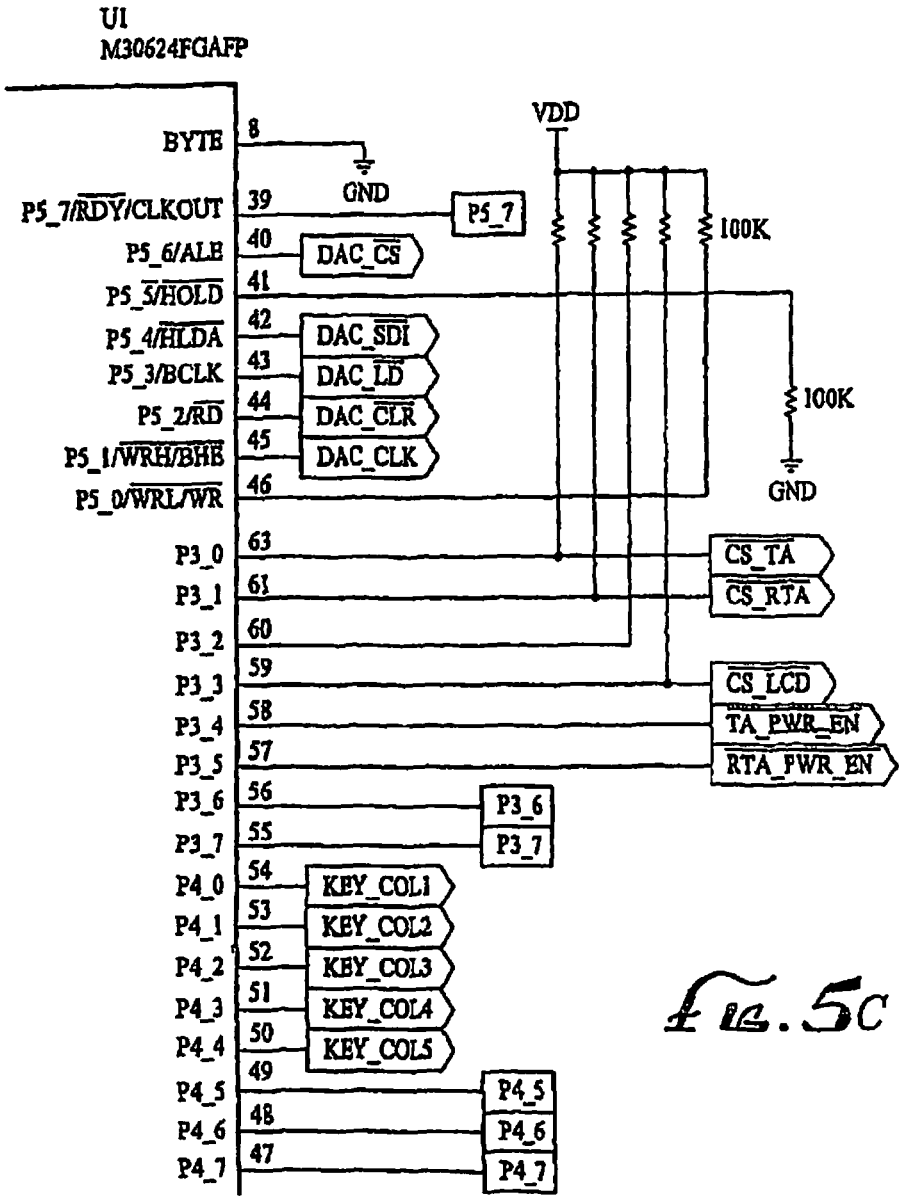
Figure 5D:
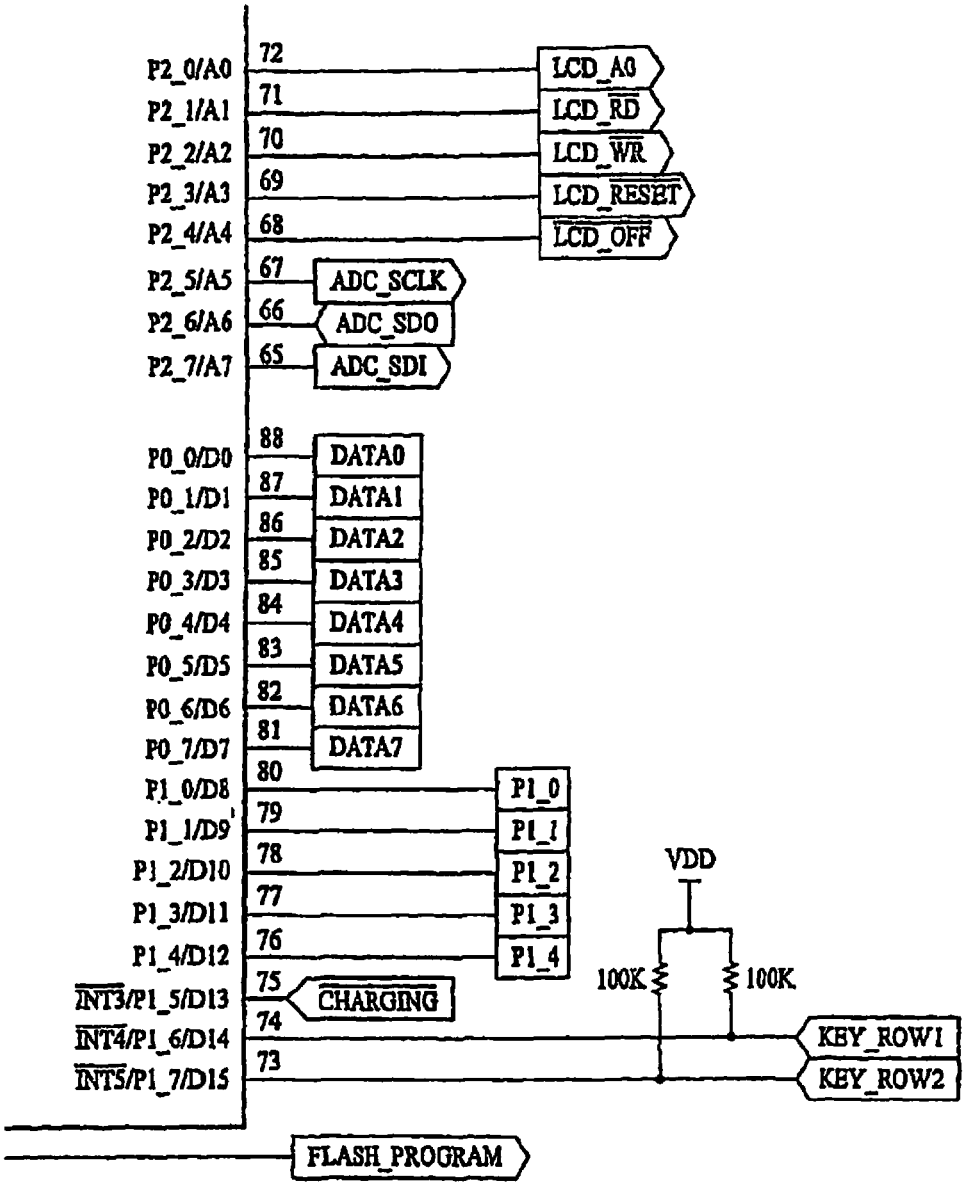
Figure 5E:
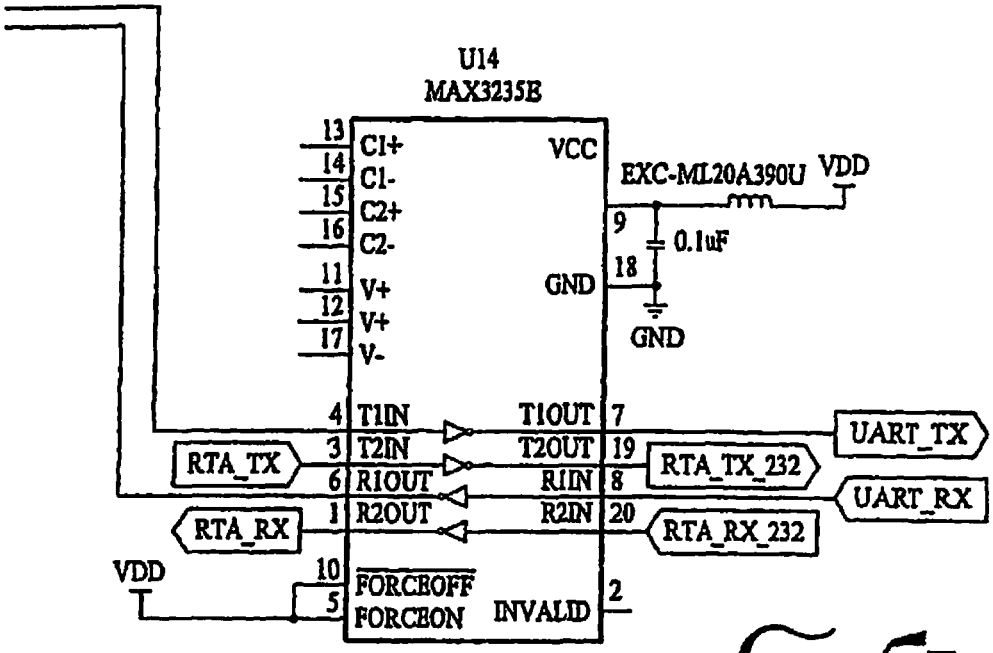
Figure 7:
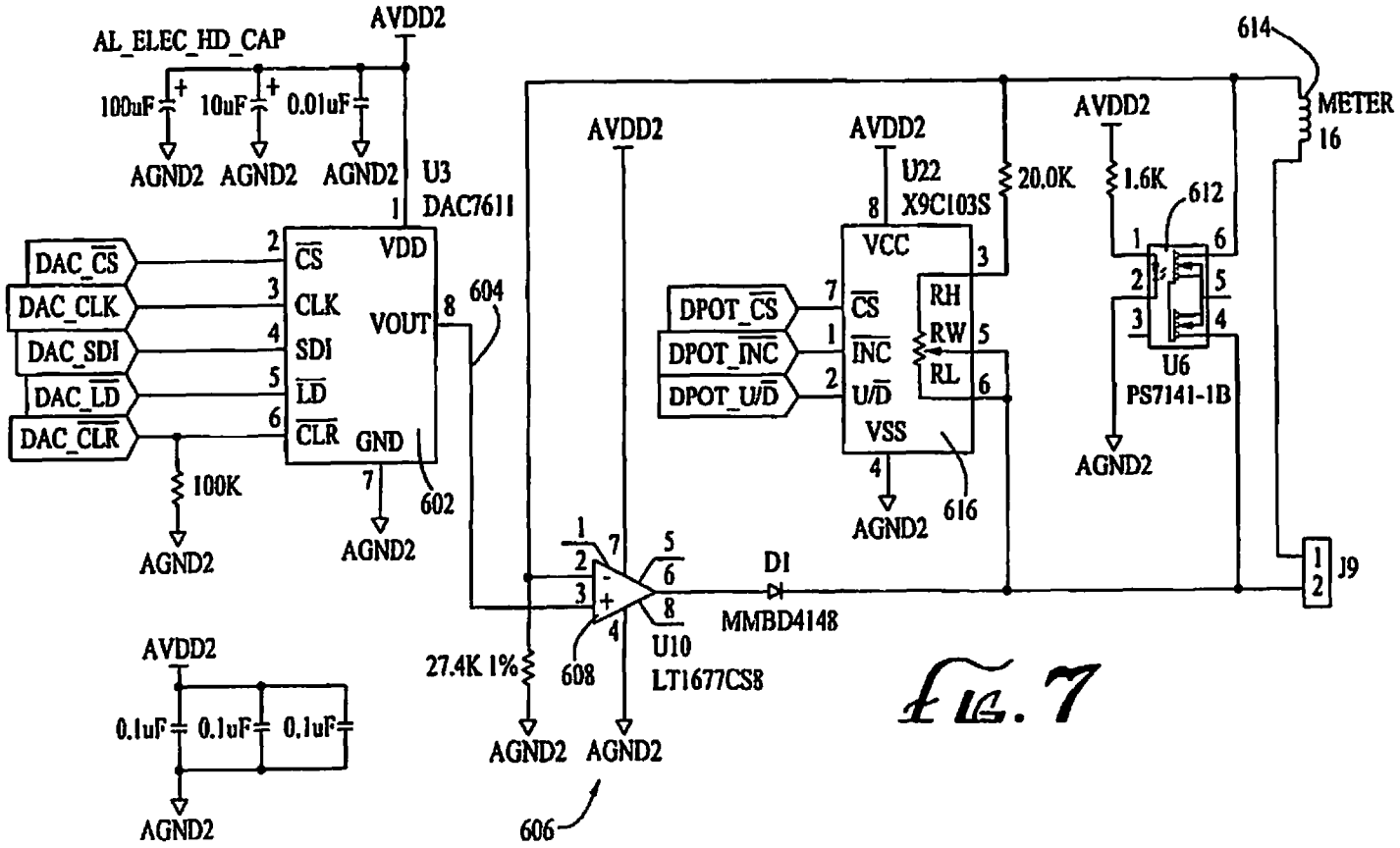

FIG. 3 hereto is a block diagram of the preferred embodiment of circuitry utilized by the device 10;

FIG. 4 hereto is a schematic illustration of the preferred front end circuitry for constructing the device of FIG. 1 in accordance with the invention;

FIG. 5 illustrates the correct arrangement of FIGS. 5A-5E that together, in turn, illustrate a block diagram schematic of a preferred central processing unit used in the device of FIG. 1;

FIG.6 is a schematic illustration of the preferred sensitivity adjustment circuitry used in the device of FIG. 1; and FIG. 7 is a schematic illustration of the preferred meter-driving circuitry used in the device of FIG. 1.

DESCRIPTION OF THE PREFERRED EMBODIMENT

FIG. 1 is a front view in perspective of a preferred embodiment Of a device that has been constructed in accordance with the invention for measuring and indicating changes in resistance of a living body. The device 10 comprises a housing 12 having a window 14 through which a meter 16 is visible. As will be explained below, the meter is utilized to display values of, and changes in, the body resistance of a person being audited by the device (hereinafter, simply "body resistance"). Those skilled in the art will recognize that displays other than the type of meter described herein are within scope of the invention.

The housing 12 includes a second window 18 for viewing a display 20. The display 20 is preferably a liquid crystal display (LCD) that selectively displays such information as the date, the time, tone arm position, tone arm movement, elapsed time during the auditing session, chosen display language and other pertinent information. Three buttons 22A-C are associated with the display 20 to select and/or change the displayed language, time, date, etc. One of the buttons is used to select a desired menu from a series of sequentially displayed menu titles. The remaining two buttons are respectively utilized to move n selection bar with respect to the menu to choose from among a plurality of listed options. The first button then functions as a select button to select the option so identified.

A second set of three buttons 28a-c is utilized to select meter sensitivities, of "low", "medium" and "high", respectively. As will be discussed in more detail below, the selected sensitivity is a function of the audited body resistance change, and a sensitivity knob 26 works in conjunction with the buttons 28a-c to provide an additional sensitivity adjustment. For that purpose, a stationary 32-segment scale is printed on the housing about the knob 26. The device is configured so that a knob setting of "32" in the "low" range selected with button 28a yields a meter sensitivity equivalent to a knob setting of "1" in the medium range selected with button 28b, and a knob setting of "32" in that medium range yields a meter sensitivity equal to a knob setting of "1" in the high range selected with button 28c. As further shown below, the low range imposes a gain of approximately 1 on the measurement signal derived from the body resistance, the medium range imposes a gain of approximately 9.5 on the signal, and the high range imposes a gain of approximately $(9.5)^2$, or 90.25, on the signal. Naturally, all of these numerical gains and relationships can be varied without departing from the spirit or scope of the invention.

The device 10 further includes a "battery test" button 29, an on/off button 31, and a "meter trim" button 33.

A rotary knob 24 is utilized to select the appropriate range for the meter 16 as described below, and is typically referred to as the "TA" knob by experienced users of these devices. The term "TA" will accordingly be used herein to refer to meter range setting from time to time. The TA knob 24 is preferably coupled to an optical encoder within the housing that produces a digital value indicative of the knob's rotational position. The rotational position of the knob may conveniently be thought of in terms of the number of degrees it has been rotated from its counterclockwise endpoint, but is conveniently discussed in terms of the TA value represented by its position. The knob is accordingly shaped at 24A to point to a TA value on a stationary, circumferentially disposed numeric scale 36 imprinted on the case 12. The scale is preferably provided with gradations marked from "0" to "6" over an arc of approximately 240°, and the knob is typically rotated clockwise from a TA value of 0.5 to a TA value of 6.5 during the auditing procedure. It should be noted that the numbers and spacing have been chosen to be consistent with prior devices such as those illustrated and described in U.S. Pat. No. 4,459,995 and that any series of numbers, letters or other markings arranged about any convenient arc could be utilized without departing from the spirit of the invention.

A pair of electrodes 30, 32 are detachably coupled to a jack 34 at the back of the housing 12, and are adapted to be held by a person being audited. Any and all numerous other methods of attachment to a living body, however, are within the scope of this invention as well. The electrodes can be of any appropriate shape. It is preferable that a audited person hold an electrode in each hand, however, and it has been found that a generally cylindrical electrode can be comfortably gripped by the audited person and is therefore preferable.

Figure 2:
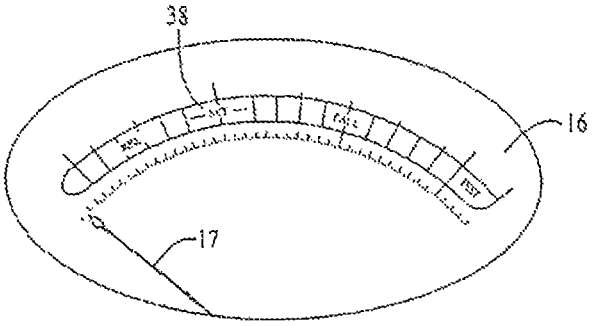
FIG. 2 is a top plan view of the preferred meter 16 used in the device of FIG. 1.

FIG. 2 is a top view of the preferred meter 16. The meter is preferably a moving-coil meter capable of reading from 0 to 100 microamps at full scale deflection, and has an arcuate scale 38 divided into sections. At approximately one-third of the distance from its left endpoint, the scale displays a small sector of arc marked "SET". In operation, and during the pre-operation calibration of the meter, its needle 17 is described as being "at SET" when the needle points to the segment of the scale labeled as "SET". The TA knob 24 is used to periodically bring the needle back to the area near SET during the auditing process, and the sensitivity of the meter is adjusted using the buttons 28a-28c and knob 26 before or during the auditing procedure to obtain appropriately meaningful needle deflections. Preferably, no more than 50 micro-amps of electrode current flows through the audited person's body. This level has been found to assure the person's comfort, while providing properly responsive needle "reads" as the person is monitored during auditing.

FIG. 3 is a block diagram of the preferred embodiment of circuitry utilized by the device 10. As shown in FIG. 3, the meter 16 is driven by an analog output signal 480 generated by a digital-analog converter 479 in response to a series of digital values 478 produced by a central processing unit 400. The central processing unit 400, in turn, is responsive to respective input signals 190, 290 and 390 from front-end circuitry 100, TA circuitry 200 and sensitivity circuitry 300.

The front-end circuitry 100 is represented schematically in FIG. 4. During the monitoring operation, it produces a digital value indicative of the electrical resistance of the audited live body. When the device is powered up, it produces calibration data for use during the monitoring operation.

The front-end circuitry 100 comprises a resistance sensing circuit 108 for producing a measurement signal indicative of body resistance, a voltage follower 110 for filtering and isolating the measuring signal from the effects of other system components, and an analog-digital converter 120 for converting the measurement signal to a digital value indicative of body resistance measured by the resistance sensing circuit.

The resistance sensing circuit is preferably of the voltage divider type electrically coupled between a positive D.C. source voltage $AV_{DD}$ and ground AGND. During the auditing session, the resistance sensing circuit comprises a 4.99 K resistor R1, the body resistance Rpc (as sensed between the electrodes 30, 32 coupled to pins 1 and 3 of jack 104), and a 45.3 K resistor R3, all coupled in series between the D.C. source $AV_{DD}$ and ground. When the monitoring electrodes have been disconnected from the jack 104, the jack is configured to electrically couple pins 2 and 3 together, placing the 4.99 k resistor R2 across the jack.

The resistor R1 is not electrically coupled directly to the electrode jack 104, but is instead coupled to it (and to body resistance $R_{pc}$) through an analog multiplexer-demultiplexer 102, preferably a Burr Brown MC14051BD. More specifically, R1 is coupled to pin X of the multiplexer/demultiplexer (hereinafter, the "multiplexer") 102. The multiplexer 102 is configured to connect its pin X to a selected pin $X_0$, $X_1$, $X_2$, $X_3$, in response to a respectively associated selection signal applied at its pins A, B, C.

The multiplexer 102 is placed in circuit with the voltage-dividing resistors for use during the calibration process described below. During normal auditing of a living body, it electrically couples pin X to pin $X_0$, placing resistor R1 in series with the body resistance $R_{pc}$. The result is an analog measurement voltage $e_o$ which varies with variances in the body resistance in accordance with the voltage-dividing equation, $$e_0 = \frac{R_3}{R_1 + R_{pc} + R_3} \times V_{DD} \qquad \text{(Eq. 1)}$$

The measurement signal $e_o$ is fed to an operational amplifier 110 configured as a voltage follower. The preferred operational amplifier is a Burr Brown LT1677CS8. The output of the operational amplifier 110 is applied to a 24 bit analog-to-digital converter 120, preferably a Burr Brown ADS 1210U, and a digital value representative of the measured body resistance is produced at its output pins SDO and SDIO to be clocked into pin 66 of the central processing unit ("CPU") 400 in response to clock pulses applied to pin SCLK.

Calibration Feature

Persons of ordinary skill in the art recognize that there can be numerous sources for error in representing body resistances $R_{pc}$ as a measurement voltages $e_o$. For example, the values of circuit resistances may vary over time and may also vary with temperature, affecting the accuracy of the voltage divider network. In addition, internal voltage levels, leakage currents and offset voltages within the solid state components of the device can vary with age and/or temperature changes and can vary from device to device within normal specified and unspecified component tolerances. Although components with extremely tight tolerances can be utilized to minimize such errors, such components are quite expensive, and the errors are still not completely eliminated. Since such errors can mask or result in false reports of small but meaningful measurement changes, devices of this type have necessarily included a calibration process intended to minimize such errors. Such prior art calibration procedures have been quite complex and have typically required the devices to be returned to the factory once each year.

In accordance with one aspect of the invention, a calibration circuit is included which can self-calibrate the device each time the device is powered up. First, an actual measurement signal $e_o$ is obtained at a number of reference points. The reference points are selected by substituting a known resistance for the body resistance $R_{pc}$. Some or all of these known resistances are standardized values which have been associated with TA values in the past. For example, a body resistance equal to 5 k-ohms has been chosen in the past as the resistance which would bring the meter's needle to SET at a TA setting of "2", a body resistance of 12.5 k-ohms would do the same for a TA value of "3", etc.

As described below, the calibration procedure herein replaces $R_{pc}$ with a 5 k-ohm resistor, a 12.5 k-ohm resistor and a short circuit so that the actual value of the measurement signal $e_o$ for each such calibration point can be obtained, digitized and temporarily stored. A model is then computed from these stored signal values for the value of the measurement signal that would place the meter on SET for each of the other TA values. During the monitoring process, the audited body resistance value is compared to the stored value that would place the meter on SET for the TA that has been dialed in, and the difference between the signal values is used to drive the meter needle, thereby compensating for the component changes described above. Naturally, the number of calibration points, as well as the TA values utilized can be varied without departing from the invention.

Accordingly, the CPU 400 sends appropriate selection signals to pins 9, 10, 11 of the multiplexor 102 upon power-up to cause its terminal X to be sequentially coupled to terminals X1, X2, and X3, respectively placing a 4.99 K resistor R2, a 12.4 K resistor R4, and a short circuit in series with resistors R1 and R3 in lieu of Rpc. The value of eo under each condition is fed to the operational amplifier 110, digitized by the converter 120 and outputted to the central processing unit 400. The above values were chosen for R2 and R4 because the TA ranges of "2" and "3" have historically been the most commonly used settings when monitoring body resistance. The short circuit condition is used to easily provide an additional data points. An open-circuit condition could be used as well.

The value of the measurement voltage is related to the resistor values and the D.C. source voltage by the equations:

$$\frac{R3}{R1+R2+R3}\times V_{DD} \text{ when terminal X1 is selected,} \quad \text{(Eq. 2)}$$

$$\frac{R3}{R1+R4+R3}\times V_{DD} \text{ when terminal X2 is selected,} \quad \text{(Eq. 3)}$$

$$\frac{R3}{R1+R3}\times V_{DD} \text{ when terminal X3 is selected,} \quad \text{(Eq. 4)}$$

If an open-circuit condition were desired, terminal X4 could be selected, yielding a measured signal of $e_{error}$, where $e_{error}$ is any non-zero voltage that is detected instead of the ideally sensed zero voltage. In the open circuit condition, the measurement voltage is theoretically zero, but errors due to component offset voltages, leakage currents and the like can cause a voltage across R3, and are consequently detected and ultimately compensated for.

Once the values of measurement voltage $e_o$ for the chosen resistor values of R2 (4.99K), R4 (12.4K) and zero (the short circuit) are obtained, the effective values of R1 and R3 are calculated by the CPU 400 from the simultaneous solution of Equations 2-4 above, using the known value of $V_{DD}$.

Once the effective values of R1 and R3 have been computed, the device next calculates the effective electrical resistance associated with the jack 104 and internal leads associated therewith. The multiplexer 102 connects its input X to terminal $X_o$. With the electrodes 30,32 disconnected from the jack 104, the jack 104 is configured to electrically couple its pins 2 and 3 together. The electrodes are accordingly disconnected during this step, so that multiplexer terminal Xo is connected to pin 2 of jack 104 and thereby to R2, R3 and ground. The value of the measurement signal $e_o$ thus obtained is offset from the value that had been obtained when R2 had been selected via multiplexor pin $X_1$ by an amount corresponding to the effective jack resistance. Since the jack resistance adds to the sensed body resistance during auditing, the value of the jack resistance is calculated and thereafter subtracted by the CPU 400 from all sensed body resistance values during auditing.

The computed values of R1, R3 and the jack resistance are used in setting the other measurement signal values which place the meter needle on SET, as previously described. Historically, for example, a TA value of 2 would ideally place the meter needle on SET when a 5K resistor was placed across the electrodes. For TA values of 3, 4, 5, the resistor values have traditionally been 12.5K, 30K and 100K. To retain consistency with prior art devices of this type, it is desirable to maintain these same nominal relationships, although those skilled in the art will recognize that this is not otherwise necessary.

Auditing

After calibration, and during monitoring of the living body, the instantaneous value of body resistance $R_{pc}$ is sensed across the electrodes 30, 32, the resulting measurement signal $e_o$ is digitized by the converter 120 and passed on to the CPU 400 where it is compared to the value corresponding to the TA then dialed in, and the difference between the two signal values is used to drive the meter needle from SET.

The CPU 400 accordingly receives two inputs thus far. First, it calculates the monitored body resistance ($R_{pc}$) from the digitized value of measurement signal in accordance with Equation 1, above, and taking the jack resistance into account. This is typically done in real time.

The CPU then subtracts a resistance value ($R_{TA}$) which it calculates from theposition of the optical encoder knob 24. In this regard, the TA knob is typically rotated during the auditing procedure to place the meter's needle on or near SET. As the TA knob is rotated, it rotates the spindle of the digital encoder 200, generating a digital value to the CPU indicative of the knob's rotational position. The digital value correlates to the TA value associated with the knob's position, which is indicated on the scale adjacent the knob. The digital position-indicative value applied to the CPU 400 is processed by the CPU to calculate a resistance value for the dialed TA position in accordance with a preferred equation:

$$R_{TA} = \frac{3}{0.00016611111 - 0.00002555556\,(TA)} \text{ where TA is the TA value.}$$

The difference between the two values is the value forms the basis for the needle-driving signal that is applied to the meter 16. The amount by which the needle is driven away from SET is a function of the magnitude of the difference. As now discussed, an adjustable "sensitivity" gain can be applied to control the degree to which a difference magnitude moves the needle. However, it will be appreciated that the difference signal, itself, is unaffected by sensitivity adjustments.

Sensitivity Feature

As previously described, the CPU 400 calculates the body resistance across the electrodes from each sampled value of the measurement voltage by subtracting the sampled body resistance value from $R_{TA}$. If the difference is "0", the processor produces a digital output value which is coupled to the meter through a digital-analog converter and places the needle of the meter on SET. If the difference is positive, the needle is driven to the right of SET. If the difference is a negative value, the needle is driven to the left of SET. If the operator changes the position of the TA knob, the monitored body resistance is compared with new values as the knob is rotated until the device's operator obtains the desired meter reading.

The distance to which the needle is driven from SET depends upon the setting of the sensitivity knob 20 (FIG. 1). The sensitivity adjustment determines the number of increments on the meter scale the needle moves for a signal change. The increments are conveniently referred to as "T's" in that they appear in the preferred meter to be a series of inverted T's (FIG. 2). Thus, the sensitivity setting determines the amount of needle movement away from SET for a given change in body resistance, and is conveniently stated as "ohms/T"; i.e., the change in body resistance required to move the needle one "T" increment on the meter scale.

Using an appropriate algorithm discussed below, one can make the readings of the meter needle more accurately indicative of the monitored body resistance changes. For example, non-linearities in the relationship can be modeled to produce a reading that has previously been missed because a linear relationship has been assumed when the relationship between needle deflection and the change in body resistance is not linear over the entire TA range. Moreover, it has been found that it is much more difficult to bring place the needle on SET at higher TA values, and to retain the needle within the meter's displayed range at higher TA values than at lower TA values. The result was that a decrease in usability at high and low TA values. It is therefore highly desirable to isolate the sensitivity adjustments from the range adjustments, which has been done as described above. Moreover, it is highly desirable to automatically decrease sensitivity at higher TA values, and to automatically increase sensitivity at low TA values to increase overall usability of the device.

Accordingly, the central processor 400 provides an automatically correcting gain factor to the meter drive signal for the purpose of substantially eliminating the possibility of masked and false readings across the usable range of TA values. The preferred gain factors are:

| For TA Values of: | The Factor Is: |
|---|---|
| $2.0 \le TA \ge 5.5$: | 1 |
| TA >5.5: | $\frac{45450.0}{\frac{3.0}{0.0001661111111 - 0.00002555555556 \times TA}} - 71941.30435$ |
| For TA <2.0: | $\frac{4999.956522}{\frac{3.0}{0.0001661111111 - 0.00002555555556 \times TA}} - 21087$ |

Consequently, the needle-driving value sent by the CPU 400 to the digital-analog converter is first multiplied by the appropriate one of the above three gain factors, in accordance with the TA value applied by the optical encoder to pin 36 of processor 400, before being applied to the converter. An optical encoder is utilized because it is not temperature sensitive, it lacks the life-limiting movable contacts of a potentiometer which suffer from frictional wear, and it produces a highly precise digital value that can be utilized by the CPU without analog-digital conversion.

FIG. 6 is a block diagram representation of the sensitivity adjustment circuitry utilized by the device in accordance with the invention. The CPU 400, preferably a Mitsubishi Electric M30624FGAQFP and illustrated in FIG. 5) receives a first sensitivity signal at pins 52-54 and 74 indicative of the button selected from the high, medium and low sensitivity range buttons 28a-c (FIG. 1), and a second sensitivity signal at pin 93 indicative of the setting of the sensitivity knob 26 (FIG.1).

The CPU 400 senses which of the three sensitivity range buttons 28a-c has been pressed at pins 52, 53, 54 and 73. The sensitivity buttons 28a-c, together with the other buttons illustrated in FIG. 1, are part of an electronic circuit matrix wherein each button is serviced by a unique pair of conductors conceptually forming the rows and columns the matrix. The pressing of the button changes the logic level of the conductor pair associated with the button, and the activation of that pair is sensed by the processor. For example, three sensitivity range button are all associated with row 1 of the matrix, and the pressing of any of those buttons accordingly changes the logic level of the conductor associated with row 1, which is monitored by pin 74 of the CPU 400. The high sensitivity range button 26a is assigned a matrix address of column 1, and the conductor associated with column 1 of the matrix accordingly undergoes a logic level change when that button is pressed, which is sensed by pin 54 of the CPU.

Thus, the CPU digitally amplifies the meter drive signal by a factor of 100 because it has sensed the appropriate logic level signals at pins 54 and 74. (As described earlier, the high sensitivity setting provides a gain of $(9.5)^2$, while the medium and low sensitivity buttons provide gains of 9.5 and 1 respectively.

Likewise, the medium sensitivity range button 28c and low sensitivity range button 28b, are respectively assigned column addresses of 2 and 3, and the conductors associated with these columns are respectively monitored by pins 52 and 53 of the CPU. Those skilled in the art will recognize that the use of digital amplification eliminates the unwanted amplification of noise the would accompany the amplification of an analog signal value, rendering small changes in body resistance more visually perceptible with the subject device.

The sensitivity knob position signal 532 is applied to pin 93 of the CPU 400, where it is internally coupled to an analog-digital converter that produces a digital value indicative of the knob's setting. As illustrated in FIG. 6, the sensitivity knob is mechanically coupled to the wiper 524A of a potentiometer 524 that is serially coupled between a 10K resistor 525 and a 10K resistor 526 in circuit between the DC source voltage VDD and ground GND. The resistor 525, potentiometer 524 and resistor 526 form a voltage divider network. The sensitivity knob position signal 532 is accordingly a DC level signal that increases as the knob is turned clockwise and the wiper moves away from ground.

The nominal unadjusted values for the sensitivity settings are inputted to the processor during factory calibration when the device is manufactured.

Meter-Driving Circuitry

FIG. 7 is a block diagram illustration of the preferred meter-driving circuitry used in a device constructed in accordance with the invention.

The output signals from the processor 400 taken at pins 40 and 42-45 are coupled to a digital-analog converter 602. The analog output signal 604 from the converter 602 is preferably coupled to a control circuit 606 that compensates for the varying ballistics of the meter movements from device to device. The control circuit 606 comprises an operational amplifier 608 that receives the output from the digital-analog converter 602 in the form of a "chip select" input, a "clock" input, a "data" input, a "load" input and a "clear" input at pins 2, 3, 4, 5, 6, respectively. When the converter 602 receives the appropriate "select" signal at pin 2, it permits the digital data at pin 4 to be clocked in at a rate determined by the clock pulse at pin 3. The resulting analog output signal 604 is produced at pin 8 and applied to a current-drive circuit 606 that drives the meter's needle electromagnetically via the meter coil 614.

The control circuit 606 comprises an operational amplifier 608, which receives the analog output signal 604 at its non-inverting input. The output of the operational amplifier 608 is partially fed back to its inverting input to a degree controlled by a digital potentiometer 616 in the feedback loop whose resistance is set by data received at pins 1, 2 from the processor 400. The digital potentiometer 610 is adjusted during the assembly process to provide a desired amount of meter dampening, and the values applied by the CPU preserve that dampening characteristic.

The meter coil 614 is shunted by an optical FET 612 that provides a short circuit across the meter coil when the device 10 is powered off. The optical FET thereby prevent electromagnetically induced current in the meter coil arising from physical jarring of the meter while the device if turned off to cause sudden and off-scale needle movement that could damage the needle.

During the factory calibration process, the processor operates under program control to display queries on the LCD display 20 (FIG. 1) so that the technician first moves the meter's needle to the far left using the buttons 22B, 22C. The technician is instructed to press the select button 22A when the meter's needle overlies the left-most "T" on the meter. The technician is then instructed to move the meter's needle to the right using the buttons 22B, 22C until the needle is on SET, and to then hit the select button 22A. In both instances, the signal value at each end of travel is then utilized by the processor to calculate the volts/"T" needed to have the needle move to the desired position.

Recordation and Playback Feature

In accordance with yet another feature of the device, digital values representing the TA value, sensitivity, and body resistance at all, or selected, instances of time during the auditing procedure can be outputted to a personal computer or other storage device through an RS232 port or other convenient interface. In practice, these values have been satisfactorily clocked out and stored at a rate of 120 Hz as a 32 bit floating point resistance value, a 16 bit sensitivity value and a 16 bit tone arm value. Later, these archived records can be inputted back into the central processor unit of the device for demonstration of the device, teaching purposes or record review. In effect, the device responds the same whether the values are being produced in real time by auditing a living body or by receiving the values from a personal computer or other storage device.

Remote TA Adjustment

Another feature of the device 10 is its preferred ability to utilize the input of a remote TA optical encoder so that the operator can comfortably operate the device 10 and make appropriate adjustments without distracting the audited subject. The remote TA optical encoder is electrically coupled to pins 29 and 30 of the CPU 400 to communicate with the CPU in the same manner as the encoder coupled to knob 24 on the housing (FIG. 1). When the CPU senses a signal at pins 29, it deactivates the optical encoder controlled by TA knob 24 by transmitting an appropriate signal to that encoder from pin 35. The remote TA encoder thereafter provides the range value to the processor until deactivated by the operator.

While the foregoing description includes detail that will enable those skilled in the art to practice the invention, it should be recognized that the description is illustrative in nature and that many modifications and variations will be apparent to those skilled in the art having the benefit of these teachings. It is accordingly intended that the invention herein be defined solely by the claims appended hereto and that the claims be interpreted as broadly as permitted in light of the prior art.

We claim:

1. A device operated by a user to monitor and indicate changes in resistance of a living body comprising:

a resistance measuring circuit having external leads for sensing the resistance of a living body placed across the external leads;

an amplifier coupled to the resistance measuring circuit for producing an analog measurement signal indicative of the sensed body resistance;

an indicator circuit for displaying visually perceivable indicia representative of sensed body resistance changes; and a digital processing unit for digitizing and digitally processing the analog measurement signal in a manner that substantially offsets effects of component aging, tolerances and temperature on measurement signal accuracy wherein the digital processing unit includes means for substituting a plurality of electrical resistance values for sensing by the amplifier in lieu of a body resistance to produce measurement signals corresponding to simulated body resistance values, said plurality simulating a plurality of body resistance values, means for digitizing the measurement signals corresponding to the simulated body resistance values, and storing in memory a resulting plurality of calibrated measurement values corresponding to the plurality of simulated body resistance values, compensation means for computing, based on the stored calibrated measurement values, calibrated measurement values to be associated with respective additional body resistance values, means for producing an indicator-driving series of digital difference values during the monitoring of the living body's resistance that represents difference between the monitored living body's digitized measurement signals and a selected user-adjustable base value, the user-adjustable base value being selected by the user from calibrated measurement values, manually positionable means operable by the user to select from the plurality of said base values, and sensitivity adjustment means for controlling a change in the indicator-driving difference values caused by a change in the monitored living body's sensed resistance, and means applying an automatic correcting gain factor to the indicator-driving value as a function of the selected base value to produce the digitally processed measurement signal, the gain-applying means applying a first non-linear gain when the selected base value corresponds to a low living body resistance value of less than approximately 5 K-ohms, and a second non-linear gain when the selected base value corresponds to a high living body resistance value of more than 100 K-ohms, the gain for the living body resistances values therebetween being essentially a constant, said first non-linear gain being more than said constant and increasing with decreasing base value, said second non-linear gain being less than said constant and [increasing] *decreasing* with increasing base value.

2. The device of claim 1 wherein the first body-resistance value is approximately 5K-ohms.

3. The device of claim 1 wherein the second body-resistance value is approximately 100K-ohms.

4. The device of claim 1 wherein the substituting means includes a multiplexer responsive to a plurality of selection signal values to respectively place a component in the resistance measuring circuit selected from the group consisting of (1) the external leads and (2) a respective one of a plurality of electrical resistors.

5. The device of claim 1 including means for automatically activating the substituting means upon powering-up of the device to produce the calibrated measurement values.

6. The device of claim 1 wherein the digital processing unit includes means for subtracting the monitored body's electrical resistance value from the selected user-adjustable base value to produce an adjusted measurement signal as the measurement signal to the indicator means, and an optical encoder coupled to the manually positionable means for producing the base value as a function of the position of the manually positionable means.

7. The device of claim 6 wherein the optical encoder is not affixed to the device, and further including communication means for communicating digital values generated by the optical encoder to the digital processing unit.

8. The device of claim 6 including means for repeatedly sampling the resistance value of the living body;

means for subtracting each sampled value from the adjusted base value to obtain the measurement signal; and sensitivity adjustment means for coupling the measurement signal to the indicator means, the sensitivity adjustment means including means for multiplying the measurement signal by a gain factor which depends on the position of the manually-adjustable means.

9. The device of claim 6 wherein the device has both an affixed and a non-affixed optical encoder, and further including communication means for communicating digital values generated by the remote digital encoder to the digital processing unit, and means for deactivating the affixed digital encoder while remote digital values from the remote digital encoder are communicated to the digital processing unit.

10. The device of claim 6 wherein the manually positionable means consists of a manually rotatable knob, and the optical encoder includes a rotatable spindle coupled to said knob and means for producing a digital output signal indicative of the spindle's position of rotation.

11. The device of claim 10 including means for adjusting the magnitude of the digital output signal from the optical output encoder prior to the subtraction of the monitored body's electrical resistance in the substantial accordance with the equation:

$$R_{TA} = \frac{3}{0.00016611111 - 0.00002555556\ (TA)}$$

where TA is the scale position of the manually positionable means, and $R_{TA}$ is the value of the output signal.

12. The device of claim 1 wherein the substituting means includes a multiplexer responsive to a plurality of selection signal values to place respective electrical resistance values in the resistance measuring circuit in lieu of a living body resistance, and wherein the digital processing unit includes means for producing the selection signals to calibrate the device.

13. The device of claim 1 wherein the substituting means includes a multiplexer responsive to a plurality of selection signal values to place a component in the resistance measuring circuit selected from the group consisting of (1) the external leads and (2) a respective one of a plurality of electrical resistance values.

14. The device of claim 1 including means for automatically activating the substituting means, the digitizing means and the compensation means prior to the monitoring of the living body.

15. The device of claim 1 wherein the manually positionable means consists of a manually rotatable knob, and an optical encoder including a rotatable spindle coupled to said knob to produce a digital output value indicative of the spindle's position.

16. The device of claim 15 wherein the magnitude of the digital output value $R_{TA}$ is in substantial accordance with the equation:

$$R_{TA} = \frac{3}{0.00016611111 - 0.00002555556\ (TA)}:$$

where: TA=the TA value at the position of the manually positionable means.

17. The device of claim 1 including means for repeatedly sampling the analog measurement signal;

means for obtaining the difference between (a) at least some of the sampled values and (b) the user-adjustable base value to obtain respective digital difference values.

18. The device of claim 1 wherein the first non-linear gain applied by the gain-applying means is in substantial accordance with the relationship expressed by the equation:

$$\text{Gain} = \frac{5000}{R_{TA} - 21087}$$

$$\text{where } R_{TA} = \frac{3}{0.00016611111 - 0.00002555556\ (\text{TA})}$$

and

TA=the TA value at the position of the manually positionable means.

19. The device of claim 1 wherein the second non-linear gain applied by the gain-applying means is in substantial accordance with the relationship expressed by the equation:

$$\text{Gain} = \frac{45450}{R_{TA} - 71941}$$

$$\text{where } R_{TA} = \frac{3}{0.00016611111 - 0.00002555556\ (\text{TA})}$$

and

TA=the TA value at the position of the manually positionable means.

20. The device of claim 1 wherein the indicator circuit includes a meter having a face, a coil for establishing a magnetic field when electric current flows through the coil, and an indicating needle deflected along said face by the magnetic field by an amount generally proportional to the amount of electric current through the coil;

means coupling an analog electrical signal representative of the processed measurement signal to the coil; and optical transistor means shunting the coil to provide essentially a short circuit around the coil when the device is unpowered to prevent electromagnetically induced current in the meter coil from physical movement of the meter to cause sudden and off-scale needle movement that could damage the needle.

21. The device of claim 1 wherein the resistance measuring circuit includes first and second electrodes respectively coupled electrically to the external leads for electrical coupling to the living body so as to impose the resistance of the living body between the electrodes;

a voltage divider circuit adapted for coupling between a D.C. source voltage and a ground reference, the resistance sensing circuit comprising:

a first circuit leg having a series circuit connection between the D.C. source voltage and the ground reference (a) a first resistor, (b) said first and second electrodes and (c) a second resistor, said first and second electrodes being reasonably connected to said circuit.

22. The device of claim 21 further including a bypass in said series circuit for selectively establishing a connection between said first and second resistors that bypasses the electrodes.

23. The device of claim 22 wherein the bypass includes a jack having a pair of terminals respectively coupled to the first and second resistors for releasably connecting said electrodes via the jack in series circuit with the first and second resistors, and for electrically coupling said first and second resistors in series circuit when the electrodes are released from their circuit connection.

24. The device of claim 23 including a third resistor, the jack electrically coupling the third resistor in series circuit between said first and second resistors when the electrodes are released from their circuit connection.

* * * * *